United States Patent [19]

Berger

[11] 4,217,454

[45] Aug. 12, 1980

[54] PROCESS FOR STEREOSELECTIVELY REDUCING INDOLE DERIVATIVES

[75] Inventor: Joel G. Berger, Verona, N.J.

[73] Assignee: Endo Laboratories, Inc., Garden City, N.Y.

[21] Appl. No.: 928,191

[22] Filed: Jul. 26, 1978

Related U.S. Application Data

[63] Continuation-in-part of Ser. No. 773,282, Mar. 1, 1977, abandoned, which is a continuation-in-part of Ser. No. 677,438, Apr. 15, 1976, abandoned.

[51] Int. Cl.$^2$ .................. C07D 471/04; C07D 471/14
[52] U.S. Cl. ....................................... 546/50; 546/85; 546/86; 546/87; 260/326.11 R; 260/326.5 B; 260/326.9
[58] Field of Search ...................... 546/85, 86, 87, 50; 260/326.11 R, 326.5 B, 326.9

[56] References Cited

U.S. PATENT DOCUMENTS

| | | | |
|---|---|---|---|
| 3,890,327 | 6/1975 | Berger | 424/267 |
| 3,932,650 | 1/1976 | Adams | 424/267 |
| 3,989,717 | 11/1976 | Heath-Brown | 260/326.9 |
| 3,991,199 | 11/1976 | Berger | 546/85 |
| 4,018,930 | 4/1977 | Berger | 424/267 |
| 4,091,102 | 5/1978 | Teller | 546/85 |
| 4,141,980 | 2/1979 | Berger | 546/87 |

*Primary Examiner*—Alan L. Rotman
*Assistant Examiner*—Natalia Harkaway

[57] ABSTRACT

Process for the stereoselective reduction of certain amino-substituted indoles and amino-substituted indole-containing structures to trans-dihydroindoles comprising the sequential steps of (1) reacting a strong acid addition salt of such an indole with a borohydride in an appropriate solvent in the absence of acid, and (2) acidifying the step (1) reaction product by which it is reduced and hydrolyzed to form the corresponding trans-dihydroindole. Many dihydroindoles so produced, for example, the trans-2-(adamantylmethyl)-=2,3,4,4a,5,9b-hexahydro-5-phenyl-1H-pyrido[4,3-b]indole, are useful as pharmaceutical materials, such as tranquilizers.

11 Claims, No Drawings

PROCESS FOR STEREOSELECTIVELY REDUCING INDOLE DERIVATIVES

CROSS REFERENCE TO RELATED APPLICATIONS

This application is a continuation-in-part of copending U.S. Pat. application Ser. No. 773,282, filed Mar. 1, 1977, now abandoned which is a continuation-in-part of U.S. Pat. application Ser. No. 677,438, filed Apr. 15, 1976, now abandoned.

BACKGROUND OF THE INVENTION

U.S. Pat. No. 4,174,453 granted Nov. 13, 1979, which is hereby incorporated by reference, filed May 22, 1978, which is a continuation-in-part of U.S. Pat. application Ser. No. 698,589, filed June 22, 1976, itself a divisional of U.S. Pat. application Ser. No. 522,145, granted Nov. 9, 1976 as U.S. Pat. No. 3,991,199, which is hereby also incorporated by reference, filed Nov. 8, 1974 (and which is a continuation-in-part of U.S. Pat. application No. 422,613, filed Dec. 16, 1973 and now abandoned) by Joel G. Berger, the inventor herein, disclosed a process for the stereoselective reduction of certain indoles of the formula:

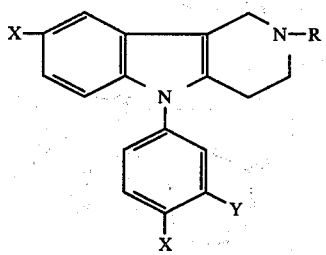

wherein
X is hydrogen or certain halogen, alkyl or alkoxy groups,
Y is hydrogen or trifluoromethyl, and
R is hydrogen or certain organic radicals
said process comprising reacting the compounds of formula I with borane/tetrahydrofuran, followed by treatment with acid.

Similarly, U.S. Pat. No. 3,932,650, granted Jan. 13, 1976 to Charles D. Adams, which is hereby incorporated by reference, discloses a process for the stereoselective reduction of certain other indoles of the formula:

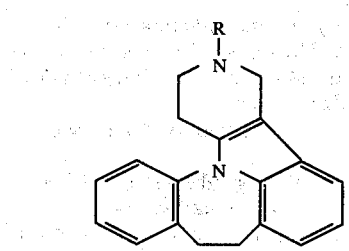

where R is certain organic radicals, said process being substantially as mentioned immediately above and in U.S. Pat. No. 3,991,199.

U.S. Pat. No. 4,091,102 which is hereby incorporated by reference, filed June 22, 1976 (and which is a continuation-in-part of U.S. Pat. application Ser. No. 606,871, filed Aug. 22, 1975, and now abandoned), granted May 23, 1978, to Sonia Ruth Teller, discloses a process for the stereoselective reduction of certain indoles of the formula:

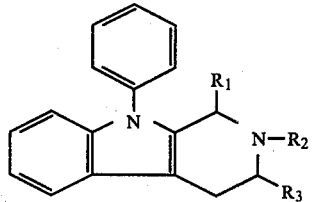

where $R_1$, $R_2$ and $R_3$ are hydrogen or certain organic radicals, the process being substantially as mentioned immediately above, and in U.S. Pat. No. 3,991,199.

The novel compounds disclosed in the above-identified patents and patent applications, which compounds heretofore have been produced by the reduction consisting of reaction with $BH_3$/THF followed by treatment with acid disclosed there, are useful as pharmaceutical materials and/or as intermediates for the synthesis of other pharmaceutical materials.

For example, the novel compounds disclosed in U.S. Pat. No. 3,890,327, which is hereby incorporated by reference, granted June 17, 1975 to Joel G. Berger, and the novel compounds disclosed in U.S. Pat. No. 4,018,930, which is hereby incorporated by reference, granted Apr. 19, 1977 (and which is a continuation-in-part of U.S. Pat. application Ser. No. 422,615, filed Dec. 6, 1973, now abandoned) by Joel G. Berger:

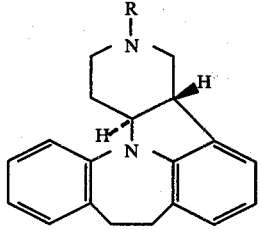

where R is hydrogen, certain organic radicals or $COOR_1$ can all be made, directly or indirectly, from certain of the compounds disclosed in U.S. Pat. No. 3,932,650, mentioned above.

The use of $BH_3$/THF suffers from several disadvantages, most notably the requirement that the primary reagent be used in large excess and the fact that this reagent is toxic, flammable and generally difficult and inconvenient to use. In addition, destruction of the excess reagent is hazardous.

SUMMARY OF THE INVENTION

In accordance with the process of the present invention, it has now been found that such a stereo-selective reduction can be accomplished by reaction of a strong acid salt of an indole, such as those of formulas I, II or III, with a borohydride in an appropriate solvent followed by either (a) dilution with water to isolate the indole-borane compound and reaction of this indole-borane compound with a strong acid, or (b) direct reaction of the borane compound with a strong acid. Suitable indole strong acid salts include those prepared from mineral acids such as HCl, $H_2SO_4$ and $H_3PO_4$ or from organic acids such as $CH_3SO_3H$ and p—CH₃—CO₆· CH₃SO₃H, H₄—SO₃H. Such a procedure eliminates the above-mentioned disadvantages of the prior art process and benefits additionally by the fact that the primary reagent of the present invention, for example, sodium borohydride, is relatively inexpensive, safe and easy to handle.

DETAILED DESCRIPTION OF THE INVENTION

The process of the present invention has rather general application in that it can be used for the stereoselective reduction of many amino-substituted indoles and amino-substituted indole-containing structures to the corresponding trans-dihydro-indoles in which the amino-substituent is a tertiary nitrogen atom ($N_b$) linked directly to three carbon atoms, one of which in turn is linked directly to the double bond to be reduced. It should be understood, of course, that other reducible sites on the subject indole or indole-containing molecule may be acted upon as well, so that if action is desired at the indole double bond only, suitable modifications to other parts of the indole or indole-containing molecule must be effected prior to the performance of the process of the present invention.

Examples of compounds which can be stereospecifically reduced to the corresponding trans-dihydro-=indoles without the incidental reduction at some other site include those of the following formulas and those compounds containing substructures of the following formulas:

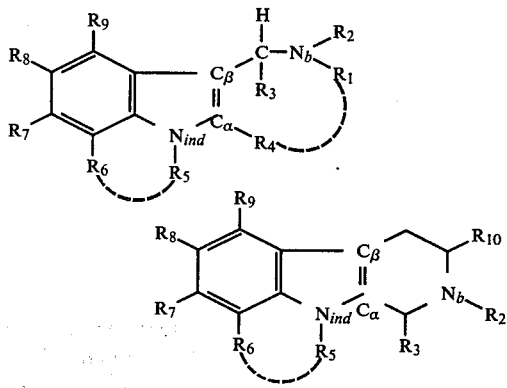

where in $R_1$ can be an alkyl of 1 through 5 carbon atoms or can be linked with $R_4$ to form an ethylene group;

$R_2$ can be an alkyl of 1 through 5 carbon atoms, benzyl, benzyl substituted with methyl, methoxy or chloro; phenethyl, 3-phenylpropyl, 3-phenylpropyl with the phenyl ring substituted with chloro, bromo, or methoxy; $C_3$–$C_5$-cycloalkyl; furfuryl; 2-thenyl; $C_4$–$C_8$ cycloalkyl=methyl; (methylcyclopropyl)methyl; (cis-2,3-dimethyl=cyclopropyl)methyl; exo-7-norcarylmethyl; (4-methyl=bicyclo[2.2.2]oct-1-yl)methyl; (bicyclo[2.2.1]hept-2=yl)methyl; 1-adamantylmethyl, or a 2-adamantylmethyl group;

$R_3$ can be hydrogen or alkyl of 1 through 4 carbon atoms;

$R_4$ can be (a) phenyl, (b) phenyl substituted with one or more halogen, $NH_2$, NHR, $N(R)_2$, OR, SR or $CF_3$ groups, (c) a carbon chain, (d) a carbon chain substituted with one or more halogen, OR, SR, $NH_2$, NHR, $N(R)_2$ or $CF_3$ groups, or (e) a carbon chain interrupted by oxygen, sulfur, or nitrogen, or can be linked with $R_1$ to form an ethylene group;

$R_5$ can be (a) hydrogen, (b) phenyl, (c) phenyl substituted with one or more halogen, $NH_2$, NHR, $N(R)_2$, OR, SR, or $CF_3$ groups, (d) a carbon chain, (e) a carbon chain substituted with one or more halogen, OR, SR, $NH_2$, NHR, $N(R)_2$ or $CF_3$ groups, or (f) a carbon chain interrupted by oxygen, sulfur, or nitrogen; or can be linked with $R_6$ to form an o-phenyleneethylene group;

$R_6$ can be linked with $R_5$ to form an o-ethylenephenylene group; or $R_6$–$R_9$ can each be independently selected from (a) hydrogen, halogen, OR, SR, $NH_2$, NHR, $N(R)_2$ or $CF_3$, (b) a carbon chain interrupted by oxygen, sulfur, or nitrogen;

$R_{10}$ can be hydrogen, methyl or ethyl; in which R can be an alkyl group of 1 through 5 carbon atoms.

The reduced products are of the following formulas:

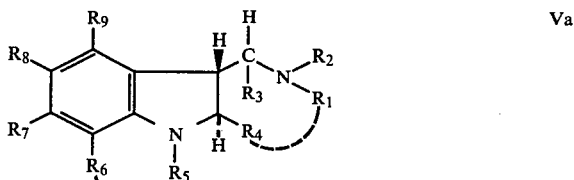

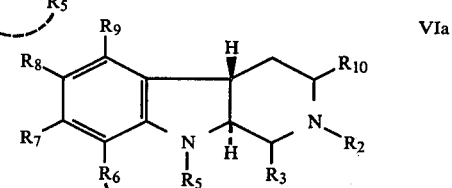

The reduction is stereoselective and when $R_4$ is other than hydrogen, all compounds produced by the present process are trans. Wherever it appears throughout the present application, the description "trans" indicates that the hydrogen atoms attached α- and β- to the indolic nitrogen ($N_{ind}$) are in trans juxtaposition to each other (cf. V and VI above). Of course, it will be understood that the double bond being reduced is the double bond between those two carbon atoms in the pyrrole ring which are α- and β- to the $N_{ind}$ and are not part of the benzene ring. These carbon atoms will be referred to as "$C_α$" and "$C_β$" respectively and the double bond linking these carbon atoms will be known as the "$C_α$-$C_β$ double bond." When $R_4$ is hydrogen, cis- trans-isomerism does not apply.

Pharmacologically useful compounds within the scope of U.S. Pat. No. 3,991,199, mentioned above, which can be produced by the present process include those of formula Va wherein $R_1$ and $R_4$ are joined and taken together are an ethylene group;

$R_2$ is benzyl; benzyl ring-substituted with methyl, methoxy, or chloro; phenethyl: 3-phenylpropyl; 3-phenylpropyl ring substituted with chloro, bromo, or methoxy; furfuryl; 2-thenyl; $C_1$–$C_5$ alkyl; $C_3$–$C_7$ cycloalkyl; $C_4$–$C_8$ cycloalkylmethyl; (methyl=cyclopropyl)methyl; (cis-2,3-dimethylcyclopropyl)=methyl; exo-7-norcarylmethyl; (4-methylbicyclo[2.2.2]=oct-1-yl)methyl; (bicyclo[2.2.1]hept-2-yl)methyl; 1-adamantylmethyl; or 2-adamantylmethyl;

$R_3$ is hydrogen;

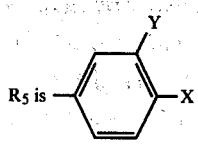

R$_6$ is hydrogen;
R$_7$ is hydrogen;
R$_8$ is X; and
R$_9$ is hydrogen;
where
when Y is —H, X is —H, —Cl, —Br, —CH$_3$, —tert-butyl, or —OCH$_3$; and
when Y is —CF$_3$, X is —H.

Compounds identified in U.S. Pat. No. 3,991,199 as being preferred are the following:
(1) trans-2,3,4,4a,5,8b-hexahydro-5-phenyl-1H-=pyrido[4,3-b]indole, because its analgesic activity is separated from its sedative activity by a 10-fold difference in dose.
(2) and (3) trans-2-(1-adamantylmethyl)-2,3,4,4a,5,9b-=hexahydro-5-phenyl-1H-pyrido[4,3-b]indole and trans-2-(2-adamantylmethyl)-2,3,4,4a,5,9b-=hexahydro-5-phenyl-1H-pyrido[4,3-b]indole, because they exhibit minor tranquilizing (anxiolytic) activity at doses which are not sedating. They also exhibit major tranquilizing (antipsychotic) activity.
(4) trans-2,3,4,4a,5,9b-hexahydro-2-(exo-7-norcaryl=methyl)-5-phenyl-1H-pyrido[4,3-b]indole, because of its potency in reducing locomotor activity.
(5), (6), (7), and (8) trans-2-ethyl-, trans-2-=cyclobutylmethyl)- and trans-2-(cyclopentyl=methyl)-2,3,4,4a,5,9b-hexahydro-5-phenyl-1H-=pyrido[4,3-b]indole, and trans-8-bromo-5-=(4-bromophenyl)-2,3,4,4a,5,9b-hexahydro-2-=methyl-1H-pyrido[4,3-b]indole because of their major tranquilizer (antipsychotic) activity.

Pharmacologically useful compounds from within the scope of U.S. Pat. No. 4,091,102, mentioned above, which can be produced by the present process include those of formula VIa wherein
R$_2$ is hydrogen, alkyl of 1 through 3 carbon atoms,
R$_3$ is hydrogen, methyl or ethyl;
R$_5$ is phenyl;
R$_6$, R$_7$, R$_8$ and R$_9$ are hydrogen; and
R$_{10}$ is hydrogen, methyl or ethyl; provided that the total number of carbon atoms in R$_2$+R$_3$+R$_{10}$ is not less than one and not more than four, and provided further that one of R$_3$ or R$_{10}$ must be other than hydrogen.

The compound identified in U.S. Pat. No. 4,091,102 as being most preferred is the compound of formula VIa wherein
R$_2$ is ethyl;
R$_3$ is methyl;
R$_5$ is phenyl; and
R$_6$, R$_7$, R$_8$, R$_9$ and R$_{10}$ are hydrogen.

Pharmacologically useful compounds from within the scope of U.S. Pat. No. 3,932,650, mentioned above, which can be produced by the present process include those of formula Va wherein:
R$_1$ and R$_4$ are joined and taken together to form an ethylene group;
R$_2$ is benzyl; benzyl ring-substituted with methyl, methoxy, or chloro; phenethyl; 3-phenylpropyl-=3-phenylpropyl ring substituted with chloro, bromo, or methoxy; furfuryl; 2-thenyl; C$_1$-C$_5$alkyl; cyclopropyl; C$_4$-C$_8$ cycloalkylmethyl; (methylcyclopropyl)methyl; exo-7-norcarylmethyl; (4-methybicyclo[2.2.2]oct-1-yl)methyl; (bicyclo=[2.2.1]hept-2-yl)methyl; 1-adamantylmethyl or 2-adamantylmethyl;
R$_3$ is hydrogen;
R$_5$ and R$_6$ are joined and taken together to form

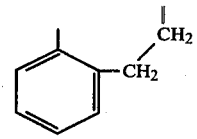

R$_7$, R$_8$, and R$_9$ are all hydrogen.

The process of the present invention comprises essentially two steps: first reacting the indole or indole-containing structure, in the form of the addition salt with a strong acid, such as hydrochloric, sulfuric, phosphoric, methanesulfonic, benzenesulfonic or 4-methylbenzenesulfonic acids with a borohydride in an appropriate solvent; and second, dilution followed by reaction with a strong acid, or direct reaction with a strong acid.

In the aforementioned copending application Ser. No. 908,572 filed May 22, 1978 by Joel G. Berger, the inventor herein, a stereoselective process for reducing the amino-substituted indole-containing structures of this invention by means of BH$_3$/THF, followed by treatment with acid, is disclosed. The success of that method is dependent on carrying out the reduction as distinct, sequential steps. Treatment with BH$_3$/THF, the first step, has to be carried out in the absence of acid, to facilitate the formation of a complex between the basic tertiary nitrogen (N$_b$) linked to the indolic C$_\alpha$–C$_\beta$ bond via a single carbon atom. When acid is added subsequent to this complex formation in the second step, protonation takes place preferably at the remaining most basic site, which happens to be the C$_\beta$. This results in the isomerization of the double bond from C$_\alpha$–C$_\beta$ to N$_{ind}$–C$_\alpha$, i.e. it transforms the borane-indole complex to the corresponding borane-indolenium complex, a charged complex having much greater affinity for hydride moieties than the unprotonated, uncharged complex. Such a hydride is delivered to the C$_\alpha$ intramolecularly by the boron atom still attached to the N$_b$. The constraints imposed by the short length of the N$_b$–B–H chain of the complex is believed to give rise to the stereoselectivity observed. Continued reaction with the acid in a vigorous manner, formally the third step, results in hydrolysis of the reduced complex to liberate the trans-dihydroindole.

In trying to overcome the above-mentioned drawbacks of the prior art process by the use of the relatively inexpensive NaBH$_4$ reagent, a reagent which moreover is safer than BH$_3$, and therefore more easily handled, two problems arose. Unlike BH$_3$, which is an electrophilic reagent (a Lewis acid), and therefore complexes readily with basic nitrogen atoms, borohydrides are nucleophilic reagents (Lewis bases), and are therefore repelled by the electron rich basic nitrogen atom. Although it is well known in the art that borohydrides can be converted in situ to BH$_3$, by means of such Lewis acids as AlCl$_3$, BF$_4$, CH$_3$SO$_3$H, H$_2$SO$_4$ or HCl, presence of any such acid in the reaction medium would lead foremost to protonation of the N$_b$, thereby preventing complex formation even if the borohydride were converted to BH$_3$. Surprisingly, it was found that by using a strong acid addition salt of the basic amine starting material, so that there was exactly one strongly acid proton for each molecule of indole to be reduced to a dihydroindole, it was possible to overcome both problems simultaneously. The protonated base was a strong enough Lewis acid to convert a borohydride to a BH$_3$, in the process vacating the N$_b$ to allow the liberated electron pair to form a complex with the nascent BH$_3$ molecule, yet since there were no more protons in solution than BH$_3$ molecules formed, and thus there was a clean sweep of all protons by the time the complex was formed, no excess acid inimical to the first step of the stereoselective reduction process described above was present any longer. Therefore, the process of the invention appears to proceed in the following manner:

(1) reaction of the indole-containing molecule in the form of the strong acid salt, which results in
   (a) generation of BH$_3$ from a borohydride, in situ, with simultaneous removal of all acidic protons;
   (b) formation, in the resulting absence of all acid, of a borane-indole complex; and
(2) acidification of the reaction product of step (1)
   (a) to isomerize this complex to a borane-indolenium complex, resulting in the stereoselective, intramolecular delivery of a hydride moiety and the formation of a borane-trans-dihydroindole complex; and
   (b) by continued vigorous treatment with acid to liberate the desired trans-dihydroindole from its borane complex.

In the above-described process, the borohydride can be any alkali metal or alkaline earth metal borohydride. Lithium borohydride and sodium borohydride are preferred. The latter is most preferred. Suitable solvents for use in the first step include ethers such as diglyme, which is diethyleneglycol dimethyl ether. The temperature of the reaction mass during the first step should be maintained between about 0° and 50° C., preferably between 25°–35° C. While one could operate outside these limits, below 0° C. the reaction proceeds too slowly to be economically practical, while above 50° C. side reactions adversely affect yield, again making such operation economically impractical. The reaction time will depend upon the other parameters chosen; however, the first step will generally proceed to completion within about 1 hour. In the first step, the reactants must be anhydrous.

Suitable solvents for use in the second step include any water-miscible ether. Diglyme, dioxane and tetrahydrofuran are preferred. Suitable acids for use in the second step include any strong mineral acid. Hydrochloric acid is preferred. The temperature of the reaction mixture during the second step should be maintained between about 65° and 125° C., preferably between 95°–105° C. The choice of both the operable and the preferred temperature ranges in this step will depend upon the physical properties of the chosen solvent, especially its boiling point. Here, too, the reaction time will depend upon the other parameters chosen; however, the second step will generally proceed to completion within about 1 and 1.5 hours.

In general, indoles of formulas V or VI are converted to a suitable salt with a strong mineral acid, preferably hydrochloric acid. This salt, as a suspension in a water-miscible ether solvent, preferably diglyme is then treated with a 1.5- to 3-fold molar excess of NaBH$_4$ as a solution in diglyme. After reacting for 30 to 60 minutes at 25°–35° C., the product amine-borane may be isolated by dilution of the reaction mixture with a large volume of water, followed by appropriate purification, if desired.

Treatment of a suspension of this amine-borane in a suitable water-miscible solvent, preferably dioxane or ethanol, followed by a short (30 to 45 minutes) period of heating (65°–100° C.) with 37% HCl gives the desired reduced products after suitable standard work-up procedures.

Alternatively, the amine-borane need not be isolated, and the suspension of crude amine-borane initially obtained may be treated directly with strong mineral acid to obtain the desired products.

EXAMPLE 1

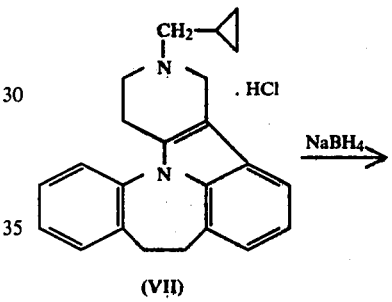

(VII)

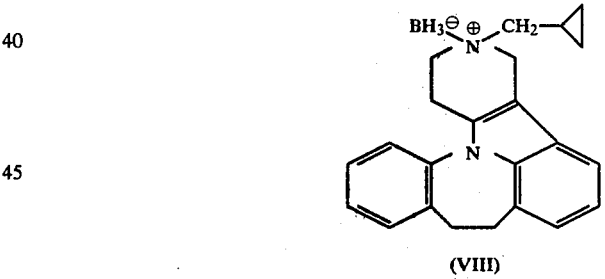

(VIII)

A solution of 3.8 grams (0.1 mole) of sodium borohydride in 100 ml of diglyme was added to a suspension of 36.4 grams of compound VII in 150 ml. of diglyme. The reaction mixture was stirred for 45 minutes at room temperature and was then poured into water. A gummy solid separated. This was washed by decantation with water several times and was then dissolved in CHCl$_3$. The solution was washed with water and dried over MgSO$_4$. Evaporation left a gum which crystallized on treatment with CHCl$_3$ and hexane. A first crop of 11.5 grams with a melting point of 126°–129° C. was obtained. The mother liquors yielded a second crop of 14.0 grams, m.p. 116°–121° C.

EXAMPLE 2

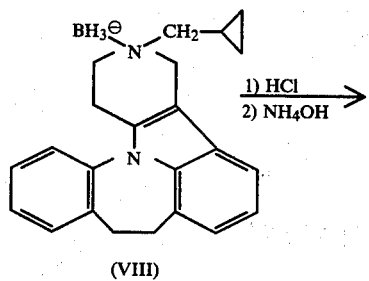

(VIII)

7 ml. of concentrated hydrochloric acid was added to a suspension of 5 grams of the amine-borane, VIII, in 25 ml. of dioxane. The solids dissolved to give a clear solution. The reaction mixture was heated at reflux for 45 minutes cooled and poured into 100 ml. of 15% ammonium hydroxide. The oily product was extracted into CHCl₃, dried over K₂CO₃, and evaporated to a yellow oil. This was dissolved in 100 ml. of hot ethanol. On cooling and scratching, a white solid precipitated, yielding 3.6 grams of IX, m.p. 149°–151° C. Mother liquors yielded another 0.2 grams, m.p. 147°–149° C.
Total yield—79%.

EXAMPLE 3

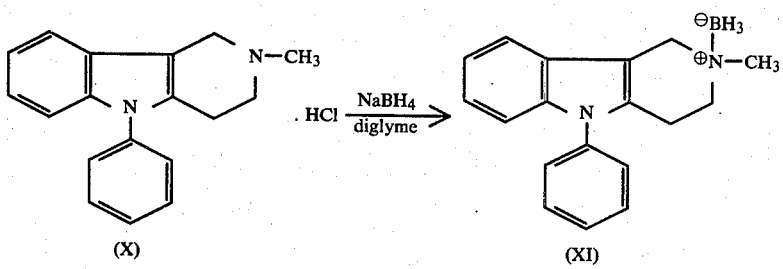

(X)  (XI)

A suspension of 25.6 grams (0.085 moles) of the hydrochloride, X, in 150 ml. of diglyme was treated with a suspension of 4.8 grams (0.125 moles) of sodium borohydride in 100 ml. of diglyme. The reaction mixture was stirred at room temperature for 1 hour, and was then poured into one liter of cold water. The resulting solids were washed with water and dried. Recrystallization from 150 ml. of 50:50 CHCl₃-hexane gave 19.5 grams of product, XI, m.p. 177°–78° C.

Analysis calc.: C, 78.27; H, 7.66; N, 10.14; B, 3.91; Found: C, 77.90; H, 7.55; N, 9.96; B, 4.14.

EXAMPLE 4

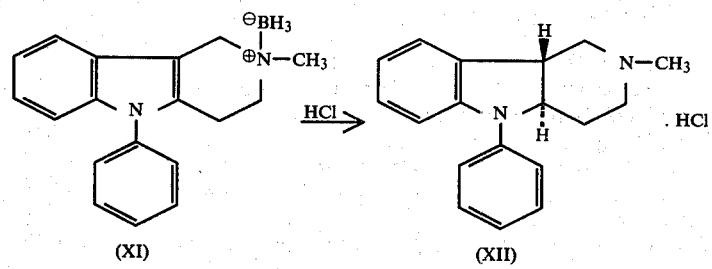

(XI)  (XII)

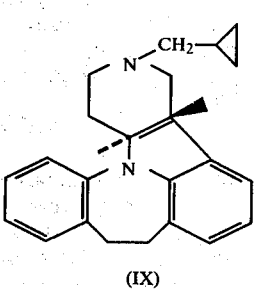

(IX)

A suspension of 2.5 grams (0.0090 moles) of the amine-borane, XI, in 50 ml. of dioxane was treated with 5 ml. of concentrated HCl, and the resulting solution was heated for 30 minutes at reflux. Excess dioxane was evaporated in vacuo, and the residue was treated with concentrated ammonium hydroxide. The product was extracted into CHCl₃, dried over K₂CO₃, and evaporated to an oil. The oil was taken up in ether and treated with ethereal hydrochloric acid. The resulting solids were filtered and dried to give 2.16 grams of the crude hydrochloride salt, XI. Recrystallization from acetone gave 1.75 grams of the product, XII, m.p. 255°–57° C.

The above reaction was repeated; however, the dioxane solution was poured into 100 ml. of 15% ammonium hydroxide, and the oily product was extracted into CHCl₃. After drying over K₂CO₃ and removal of the solvent in vacuo, the residual oil was taken up in acetone and treated with ethereal hydrochloric acid. The hydrochloride salt crystallized out and was filtered and dried, yielding 2.05 grams of product, XII.

EXAMPLE 5

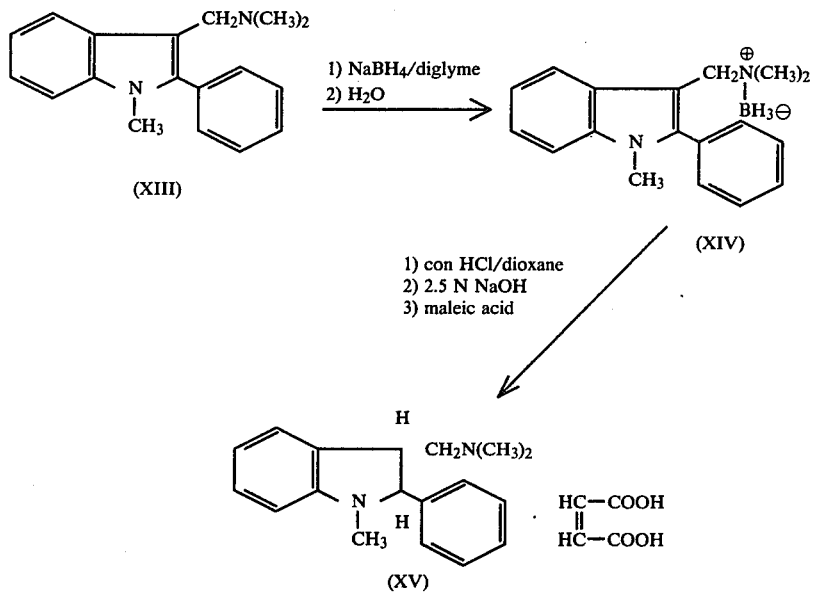

A suspension of NaBH$_4$ (400 mg., 10.5 mmol) in 20 ml. of diglyme was slowly added to a stirred suspension of XIII-hydrochloride (3.0 g., 9.9 mmol.) in 20 ml. diglyme. Gas evolution occurred during the course of the addition, and a voluminous precipitate formed. The mixture was stirred for 30 min. and then poured into water. The precipitated solids were filtered, washed with water and dried to give 2.5 g. (90%) of product m.p. 203°–206.5°. Recrystallization from CHCl$_3$-hexane gave colorless rods, m.p. 209.5–211°.

Analysis calc. C$_{18}$H$_{23}$N$_2$B: C, 77.71; H, 8.33; N, 10.07; B, 3.89.

Found: C, 77.45; H, 8.62, N, 10.12; B, 3.92.

A suspension of N,N-dimethyl-(1-methyl-=2-phenylindol-3-yl)methylamine, compound with borane (XIV) (1.4 g.) in 25 ml. of dioxane was treated with 20 ml. concentrated hydrochloric acid, then heated for 1 hour at reflux. The clear solution was concentrated in vacuo to remove most of the dioxane, diluted with 100 ml. water, and extracted with ether. The aqueous solution was basified with 2.5 N NaOH, and the oily product extracted into ether. The ether extract was washed with water, dried over K$_2$CO$_3$, and evaporated to give 1.2 g. of a colorless oil, from which a maleate was prepared, which, after recrystallization from acetone-ether melted 139.5°–143°.

Annalysis calc. C$_{18}$H$_{22}$N$_2$·C$_4$H$_4$O$_4$: C, 69.09; H, 6.85; N, 7.33.

Found: C, 69.05; H, 6.82; N, 7.27.

I claim:

1. A process for the stereoselective reduction of an indole compound selected form the group consisting of a compound having one of the following formulas:

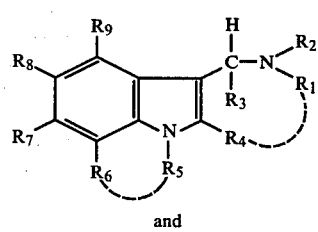

and

-continued wherein

R$_1$ can be an alkyl of 1 through 5 carbon atoms or can be linked with R$_4$ to form an ethylene group;

R$_2$ can be an alkyl of 1 through 5 carbon atoms, benzyl, benzyl substituted with methyl, methoxy or chloro; phenethyl, 3-phenylpropyl, 3-phenylpropyl with the phenyl ring substituted with chloro, bromo, or methoxy; C$_3$-C$_5$-cycloalkyl; furfuryl; 2-thenyl; C$_4$-C$_8$ cycloalkyl=methyl;(methylcyclopropyl)methyl; (cis-2,3-dimethylcyclo=propyl)-methyl; exo-7-norcarylmethyl; (4-methylbicyclo=[2.2.2]oct-1-yl)methyl; (bicyclo[2.2.1.]hept-2-yl)methyl; 1-adamantylmethyl, or a 2-adamantylmethyl group;

R$_3$ can be hydrogen or alkyl of 1 through 4 carbon atoms;

R$_4$ can be (a) phenyl, (b) phenyl substituted with one or more halogen, NH$_2$, NHR, N(R)$_2$, OR, SR or CF$_3$ groups, (c) a carbon chain, (d) a carbon chain substituted with one or more halogen, OR, SR, NH$_2$, NHR, N(R)$_2$ or CF$_3$ groups, or (e) a carbon chain interrupted by oxygen, sulfur, or nitrogen, or can be linked with R$_1$ to form an ethylene group;

R$_5$ can be (a) hydrogen, (b) phenyl, (c) phenyl substituted with one or more halogen, NH$_2$, NHR, N(R)$_2$, OR, SR, or CF$_3$ groups, (d) a carbon chain, (e) a carbon chain substituted with one or more halogen, OR, SR, NH$_2$, NHR, N(R)$_2$ or CF$_3$ groups, or (f) a carbon chain interrupted by oxygen, sulfur, or nitrogen, or can be linked with R$_6$ to form an o-phenyleneethylene group;

R$_6$ can be linked with R$_5$ to form an o-ethylenephenylene group; or $R_6-R_9$ can each be independently selected from (a) hydrogen, halogen, OR, SR, $NH_2$, NHR, $N(R)_2$ or $CF_3$, (b) a carbon chain interrupted by oxygen, sulfur, or nitrogen;

$R_{10}$ can be hydrogen, methyl or ethyl; in which R can be an alkyl group of 1 through 5 carbon atoms. which comprises the sequential steps of:

(a) reacting a strong acid addition salt of the indole compound in which the strong acid which forms the addition salt is selected from the group consisting of hydrochloric, sulfuric, phosphoric, methanesulfonic, benzenesulfonic and 4-methylbenzene sulfonic acids with a borohydride of an alkali metal or alkaline earth metal in an appropriate solvent in the absence of acid; and (b) acidifying the reaction product of step (a) with a mineral acid by which it is reduced and hydrolyzed to form the corresponding trans-dihydroindole.

2. The process of claim 1 in which the reaction mixture for step (a) is diluted with water, by which indoleborane compound is isolated prior to acidification with strong acid.

3. The process of claim 1 in which the borohydride is sodium borohydride.

4. The process of claim 1 in which the solvent is diglyme.

5. The process of claim 1 in which the strong acid is hydrochloric acid.

6. The process of claim 1 in which the acidification step is carried out in dioxane solvent.

7. The process of claim 1 in which step (a) is carried out at 25°-35° C.

8. The process of claim 1 in which the hydrolysis of step (b) is carried out at 65°-125° C.

9. The process of claim 1 in which the indole compound corresponds to the formula:

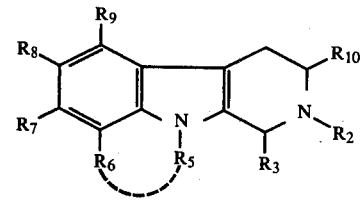

wherein $R_1$ and $R_4$ are joined and taken together are an ethylene group;

$R_2$ is benzyl; benzyl ring-substituted with methyl, methoxy, or chloro; phenethyl: 3-phenylpropyl; 3-phenylpropyl ring substituted with chloro, bromo, or methoxy; furfuryl; 2-thenyl; $C_1-C_5$ alkyl; $C_3-C_7$ cycloalkyl; $C_4-C_8$ cycloalkylmethyl; (methylcyclopropyl)methyl; (cis-2,3-dimethylcyclopropyl) methyl; exo-7-norcarylmethyl; (4-methylbicyclo[2.2.2]=oct-1-yl)methyl; (bicyclo[2.2.1]hept-2-yl)methyl; 1-adamantylmethyl; or 2-adamantylmethyl;

$R_3$ is hydrogen;

$R_5$ is

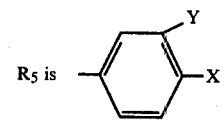

$R_6$ is hydrogen;
$R_7$ is hydrogen:
$R_8$ is X; and
$R_9$ is hydrogen;
wherein
when Y is —H, X is —H, —Cl, —Br. —$CH_3$, -tert-butyl, or —$OCH_3$; and
when Y is —$CF_3$, X is —H.

10. The process of claim 1 in which the indole compound corresponds to the formula:

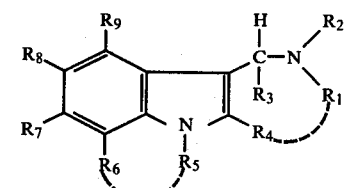

wherein $P_2$ is hydrogen, alkyl of 1 through 3 carbon atoms,
$R_3$ is hydrogen, methyl or ethyl;
$R_5$ is phenyl;
$R_6$, $R_7$, $R_8$ and $R_9$ are hydrogen; and
$R_{10}$ is hydrogen, methyl or ethyl; provided that the total number of carbon atoms in $R_2+R_3+R_{10}$ is not less than one and not more than four, and provided further that one of $R_3$ or $R_{10}$ must be other than hydrogen.

11. The process of claim 1 in which the indole compound corresponds to the formula:

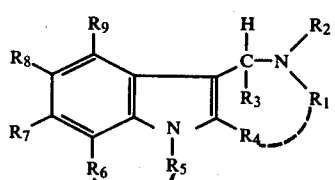

wherein $R_1$ and $R_4$ are joined and taken together to form an ethylene group;

$R_2$ is benzyl; benzyl ring-substituted with methyl, methoxy, or chloro; phenethyl; 3-phenylpropyl=3-phenylpropyl ring substituted with chloro, bromo, or methoxy; furfuryl; 2-thenyl; $C_1-C_5$ alkyl; cyclopropyl; $C_4-C_8$ cycloalkylmethyl; (methylcyclopropyl)methyl; exo-7-norcarylmethyl; (4-methylbicyclo[2.2.2]oct-1-yl)methyl; (bicyclo=[2.2.1]hept-2-yl)methyl; 1-adamantylmethyl or 2-adamantylmethyl;

$R_3$ is hydrogen;

$R_5$ and $R_6$ are joined and taken together to form

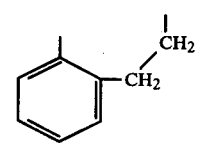

$R_7$, $R_8$, $R_9$ are all hydrogen.